(12) United States Patent
Kroll et al.

(10) Patent No.: US 6,199,427 B1
(45) Date of Patent: Mar. 13, 2001

(54) APPARATUS AND METHOD FOR TESTING LEAF SPRINGS

(75) Inventors: William P. Kroll, Medina; Randie Evenson, Brooklyn Center, both of MN (US)

(73) Assignee: Intercomp Company, Minneapolis, MN (US)

( * ) Notice: Subject to any disclaimer, the term of this patent is extended or adjusted under 35 U.S.C. 154(b) by 0 days.

(21) Appl. No.: 09/205,548

(22) Filed: Dec. 3, 1998

Related U.S. Application Data

(60) Provisional application No. 60/067,532, filed on Dec. 4, 1997.

(51) Int. Cl.[7] .................................................. G01L 1/04
(52) U.S. Cl. ................................................................ 73/161
(58) Field of Search .............................. 73/161, 862.381, 73/862.391

(56) References Cited

U.S. PATENT DOCUMENTS 4,215,754  *  8/1980  Hagedorn et al. ................... 177/137
5,161,628  * 11/1992  Wirth ..................................... 177/137
5,212,657  *  5/1993  Uchikawa et al. ..................... 702/42

* cited by examiner

Primary Examiner—Max Noori
(74) Attorney, Agent, or Firm—Skinner and Associates

(57) ABSTRACT

A leaf spring test apparatus, generally comprising a frame constructed and arranged to support a first end and a second end of a leaf spring, a force applicator disposed on the frame for applying a force to a predetermined area of the leaf spring, a force measurement gauge connected to the force applicator to gauge the amount of force applied to the leaf spring by the force applicator, and a distance measurement gauge connected to the leaf spring to gauge movement of the leaf spring upon the application of force by the force applicator to the leaf spring. A method for testing and measuring the spring rate of leaf springs, comprising the steps of installing a leaf spring on a leaf spring test apparatus, zeroing a leaf spring test apparatus, pumping a jack on the leaf spring test apparatus to raise the leaf spring a desired distance, and reading a force measurement gauge.

21 Claims, 10 Drawing Sheets

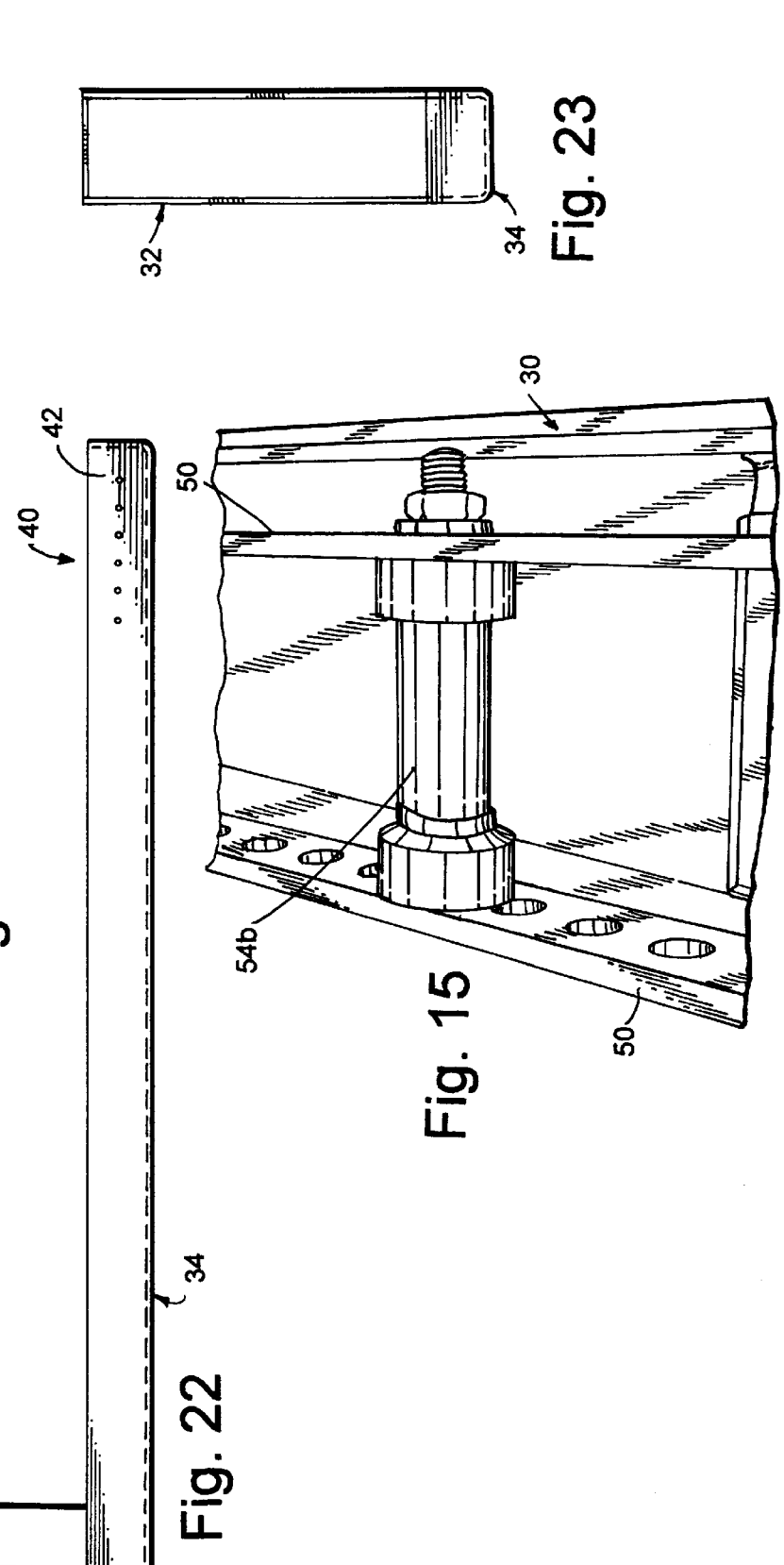

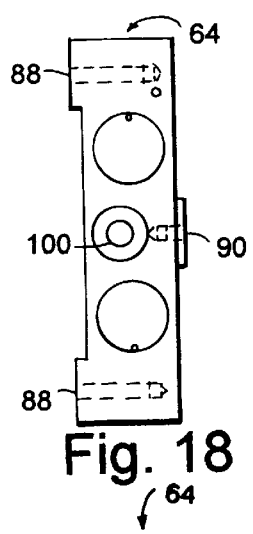
Fig. 18
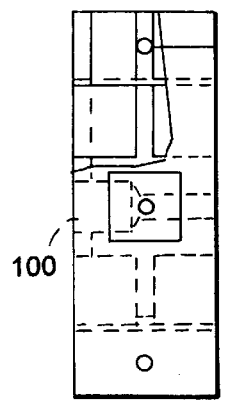
Fig. 19
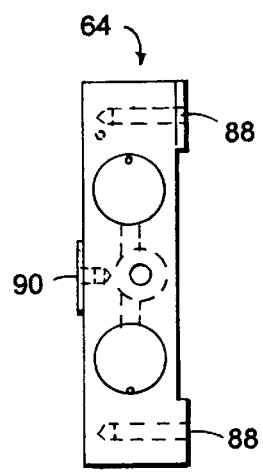
Fig. 20
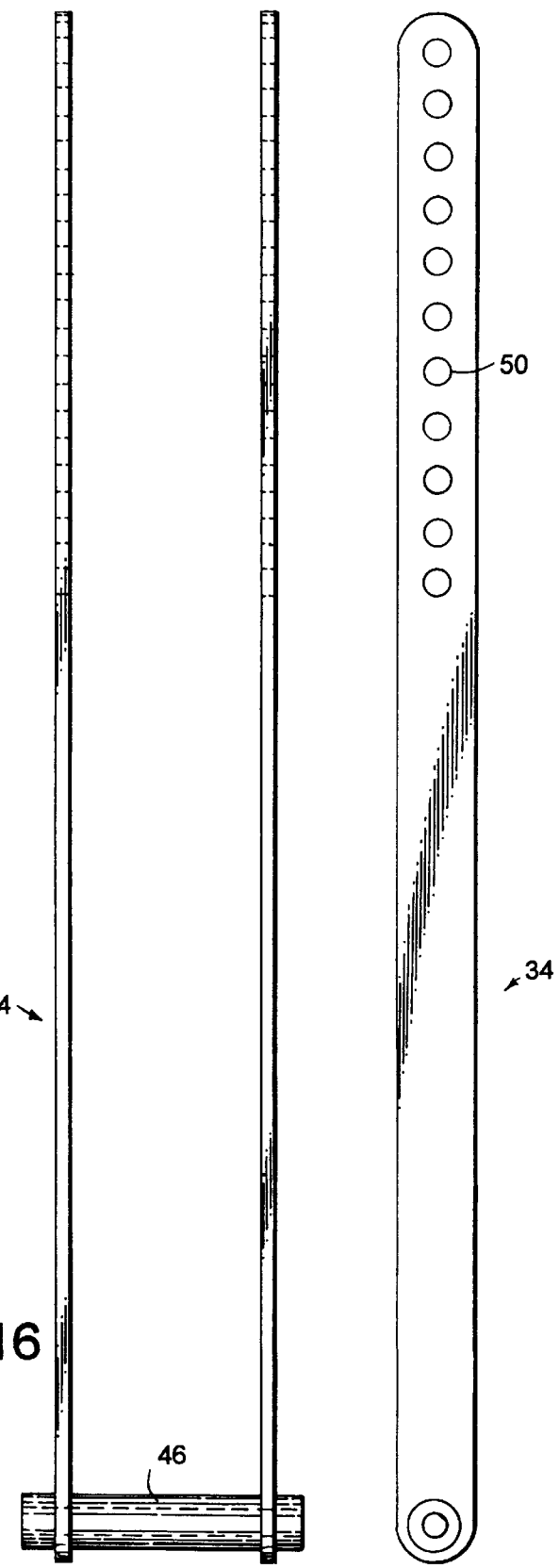
Fig. 16
Fig. 17

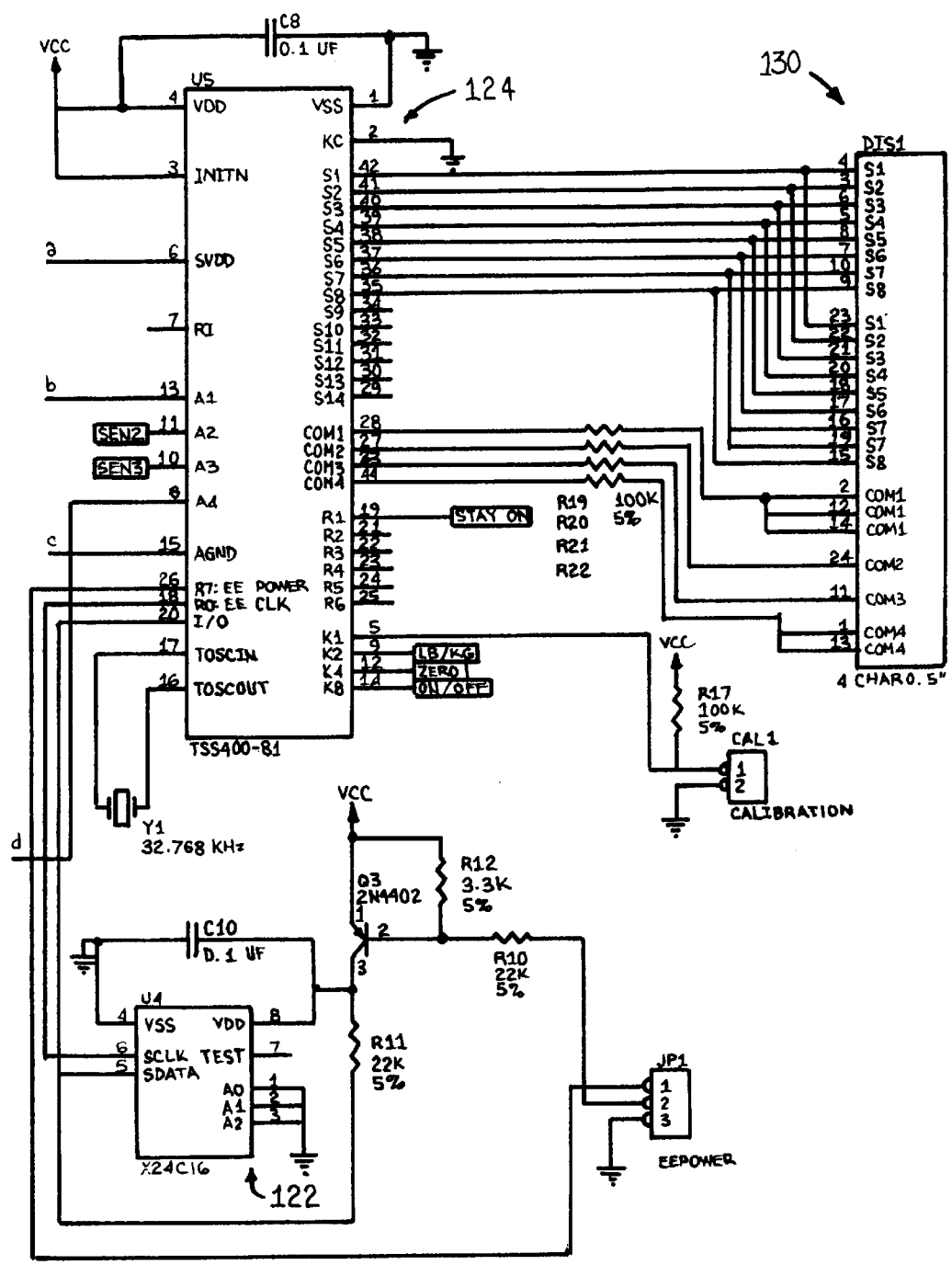
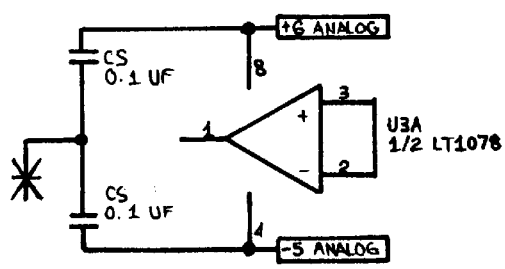
Fig. 24b

APPARATUS AND METHOD FOR TESTING LEAF SPRINGS

CROSS-REFERENCE TO RELATED APPLICATIONS, IF ANY

This application claims the benefit under 35 U.S.C. §119(e) of co-pending provisional application Ser. No. 60/067,532, filed Dec. 4, 1997.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to testing apparatus and methods. More particularly, the invention relates to electromechanical testing apparatus for measuring the spring rate of leaf springs used on automobiles.

2. Background Information

Balancing a car optimizes performance, particularly the cornering characteristics of a racing class automobile. The traction, adherence or grip between the tires and the track at each end of a car is proportional to the percentage of the weight at that end of the car. A car's grip is optimized when both the front tires and the rear tires begin to slide at the same time and at the same rate, resulting in the car having responsive, near-neutral handling characteristics. However, if the front tires slide first, the car tends to understeer and slide off of the track, and if the rear tires slide first, the car tends to oversteer and spin.

Numerous factors contribute to the near-neutral handling characteristics of a balanced car, including tires, wheel alignment, suspension, weight distribution, center of gravity and aerodynamics. A properly suspended car has more braking and acceleration control when the car is moving in a straight line and more steering control when the car is maneuvering around corners. A leaf spring suspension exerts resistance against up and down movement by the flexing action of leaf springs. One end of a leaf spring is rigidly mounted to the frame as both the axle end and the shackle location of the leaf spring freely move with the rising and falling of the wheel. The leaf spring flexes and absorbs shocks when the wheel rises.

Leaf springs have a spring rate that identifies the amount of resistance that it provides against up and down movement. This spring rate may change over time and may change because of use. It is therefore desirable to be able to accurately measure the spring rate of leaf springs in order to calculate the resistant force, balance the car, and ultimately improve the handling characteristics of the car.

Applicant's invention provides an apparatus and method for testing and measuring the spring rate of leaf springs which is believed to constitute an improvement over existing technology.

BRIEF SUMMARY OF THE INVENTION

The present invention provides an apparatus and method for testing leaf springs. The leaf spring test apparatus generally comprises a frame constructed and arranged to support both a first and second end of a leaf spring, a force applicator disposed on the frame for applying a force to a predetermined area of the leaf spring, a force measurement gauge for gauging the amount of force applied to the leaf spring by the force applicator, and a distance measurement gauge for gauging movement of the leaf spring upon the application of force by the force applicator.

The leaf spring test apparatus accurately rates leaf springs because it closely approximates the actual installed conditions of leaf springs on a car. The leaf spring is rigidly mounted to the car at the frame end and is free to move at the axle end and the shackle location. The leaf spring test apparatus accurately gauges the spring rate of all commonly used leaf springs using a load cell and an electronic digital indicator. It is anticipated that the leaf spring test apparatus can be modified within the teachings of the present invention to accurately gauge the applied force and movement to appropriately rate uncommon leaf springs that are currently manufactured or any leaf springs that may be developed.

The features, benefits and objects of this invention will become clear to those skilled in the art by reference to the following description, claims and drawings.

BRIEF DESCRIPTION OF THE SEVERAL VIEWS OF THE DRAWING

FIG. 15 is a perspective view of a small bushing extending between opposite sides of the second support for the apparatus of FIG. 1.

FIG. 16 is a top view of the second support for the apparatus of FIG. 1.

FIG. 17 is a side view of the second support shown in FIG. 16.

FIG. 18 is a side view of the load cell for the apparatus of FIG. 1.

FIG. 19 is a bottom view of the load cell shown in FIG. 18.

FIG. 20 is an opposite side view of the load cell shown in FIG. 18.

FIG. 21 is a top view of the base and first support for the apparatus of FIG. 1.

FIG. 22 is a side view of the base and first support shown in FIG. 21.

FIG. 23 is an end view of the base and first support shown in FIG. 21.

DETAILED DESCRIPTION

Figure 1:
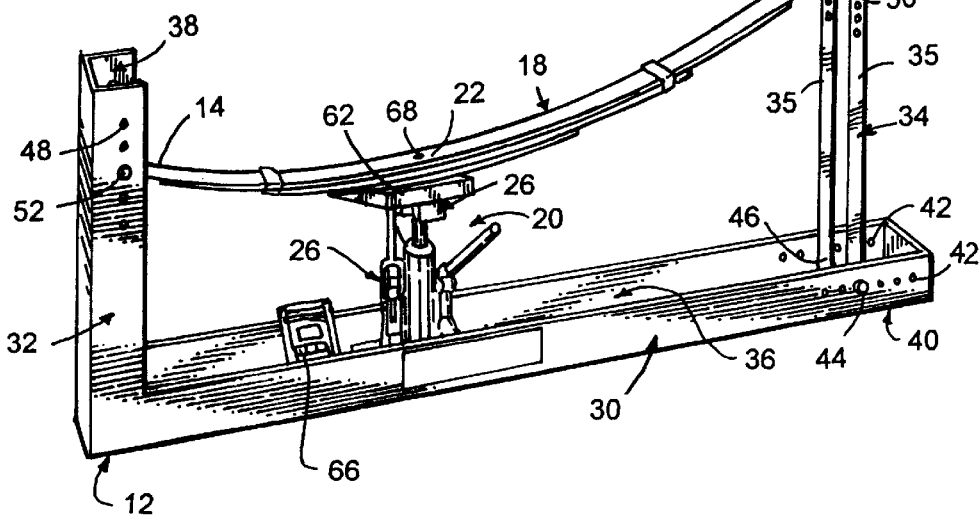
FIG. 1 is a perspective view of the apparatus for testing torsion bars of the present invention.
Figure 2:
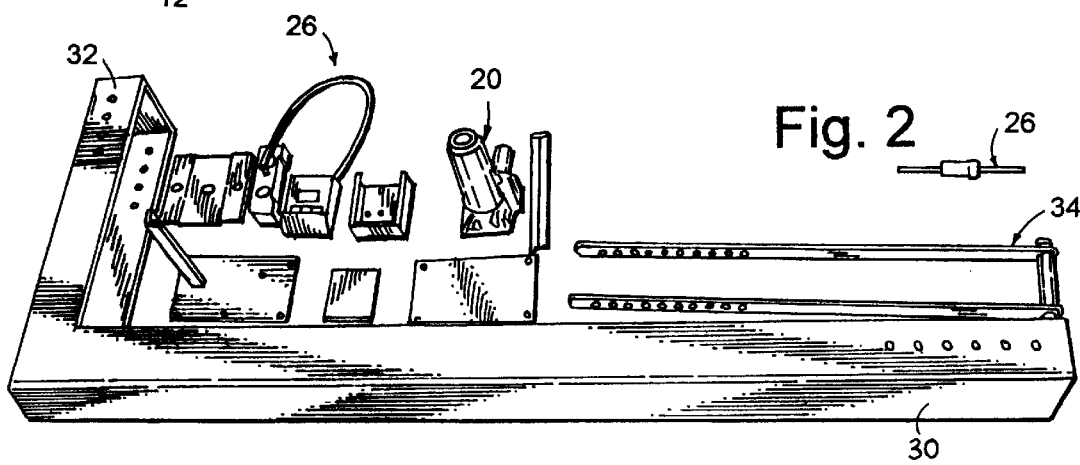
FIG. 2 is a perspective view of a disassembled apparatus of FIG. 1.
Figure 3:
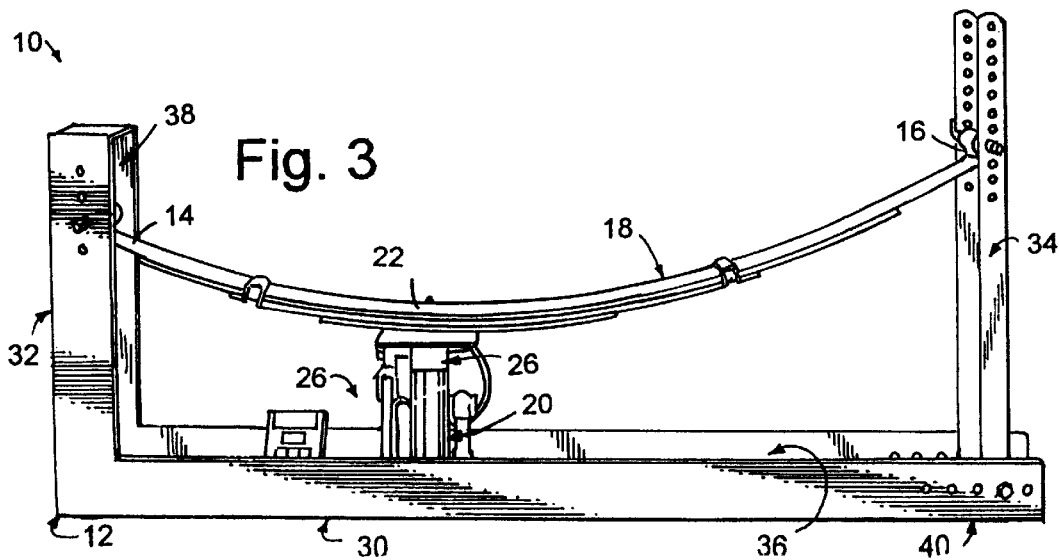
FIG. 3 is a side view of the apparatus of FIG. 1.
Figure 4:
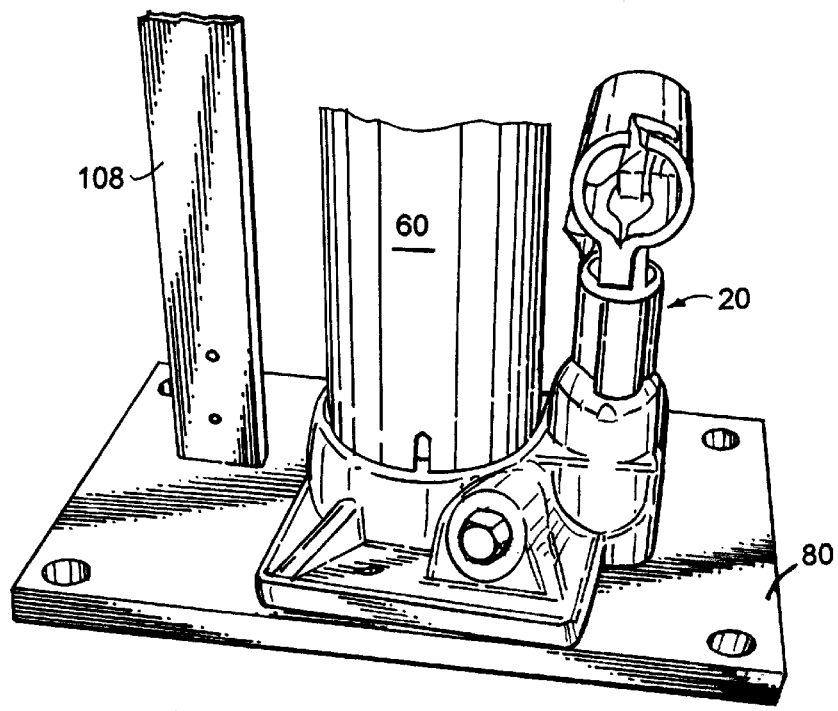
FIG. 4 is a partial perspective view of the force applicator for the apparatus of FIG. 1.
Figure 5:
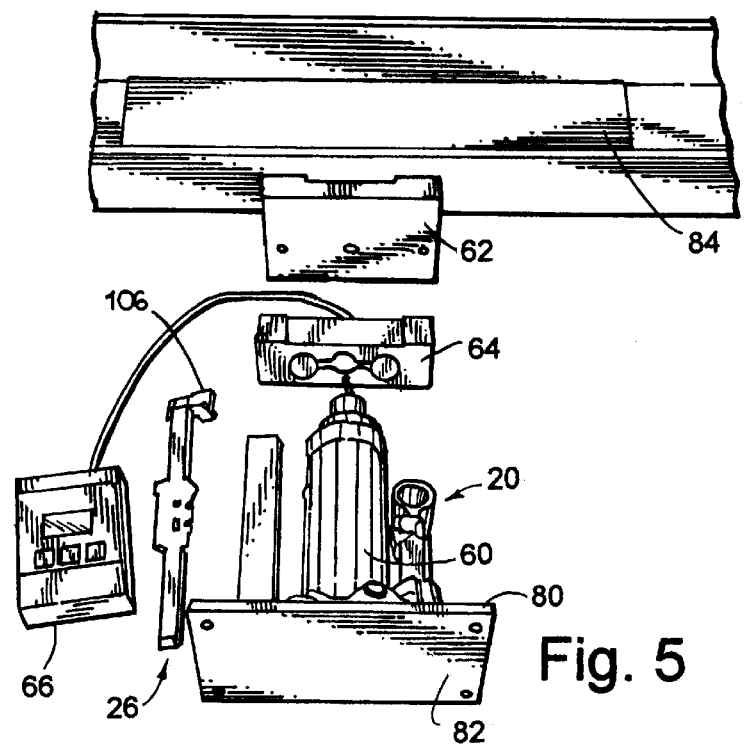
FIG. 5 is a perspective view of a partially disassembled force applicator, force measurement gauge, and distance measurement gauge for the apparatus of FIG. 1.
Figure 6:
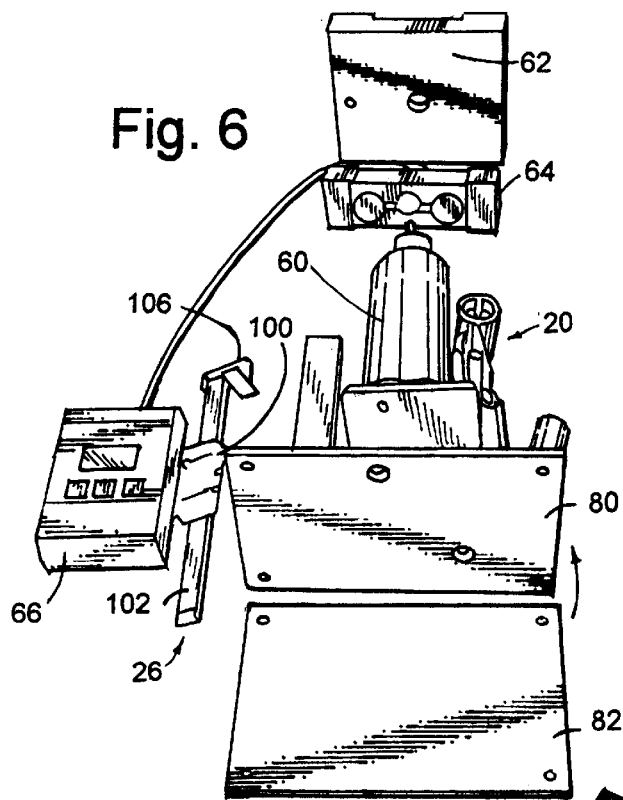
FIG. 6 is another perspective view of a partially disassembled force applicator, force measurement gauge, and distance measurement gauge for the apparatus of FIG. 1.
Figure 7:
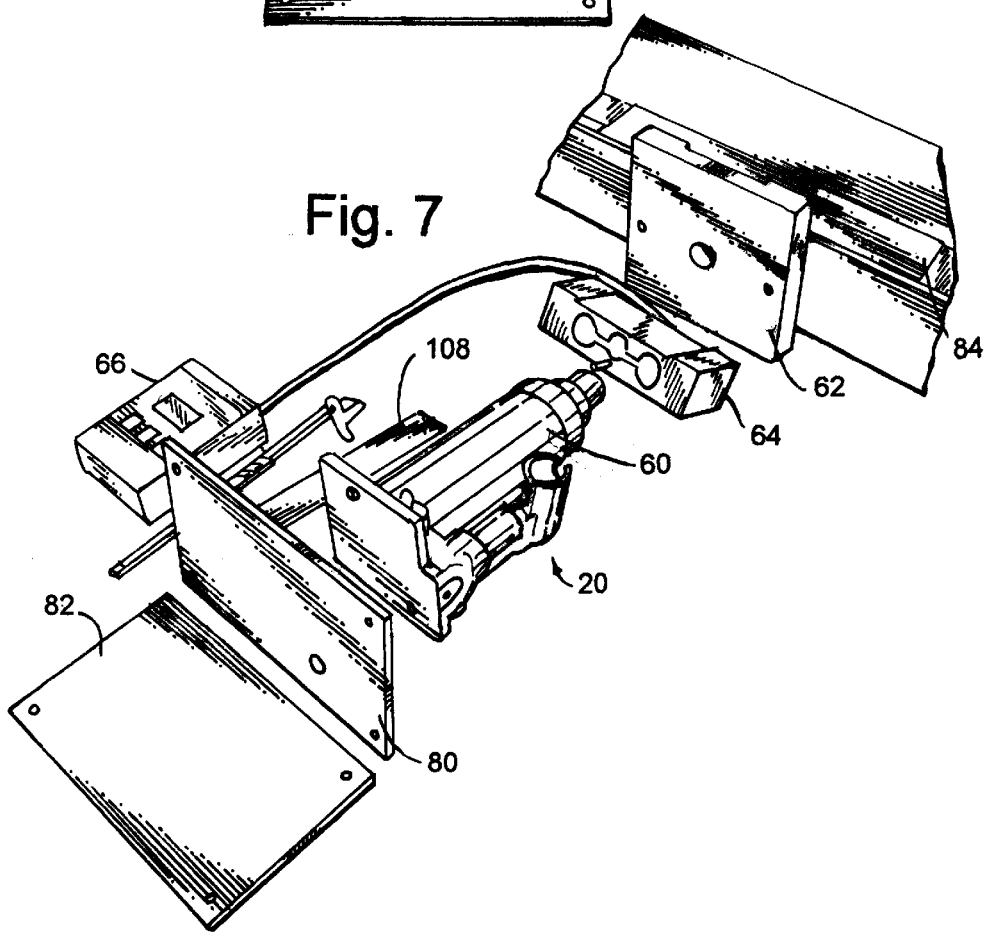
FIG. 7 is another perspective view of the partially disassembled force applicator, force measurement gauge, and distance measurement gauge shown in FIG. 6.
Figure 8:
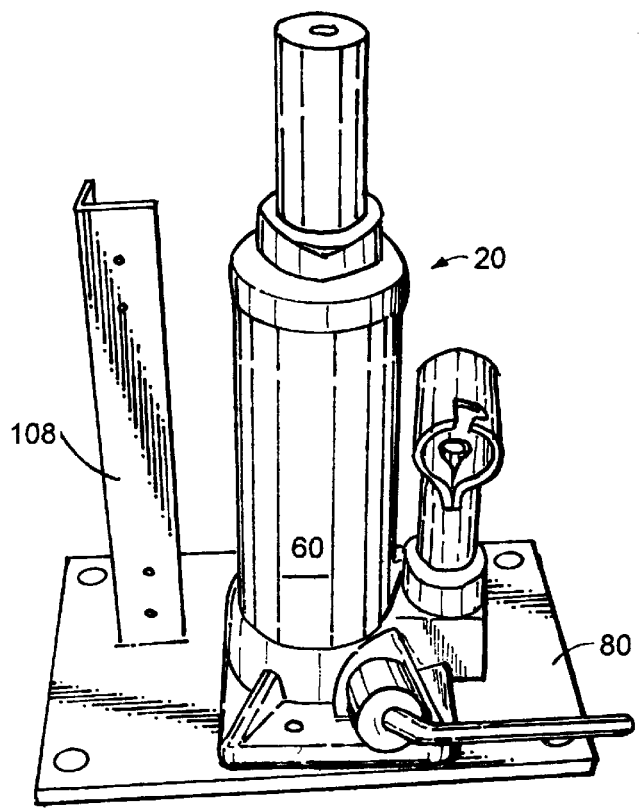
FIG. 8 is a perspective view from the top of the force applicator for the apparatus of FIG. 1.
Figure 9:
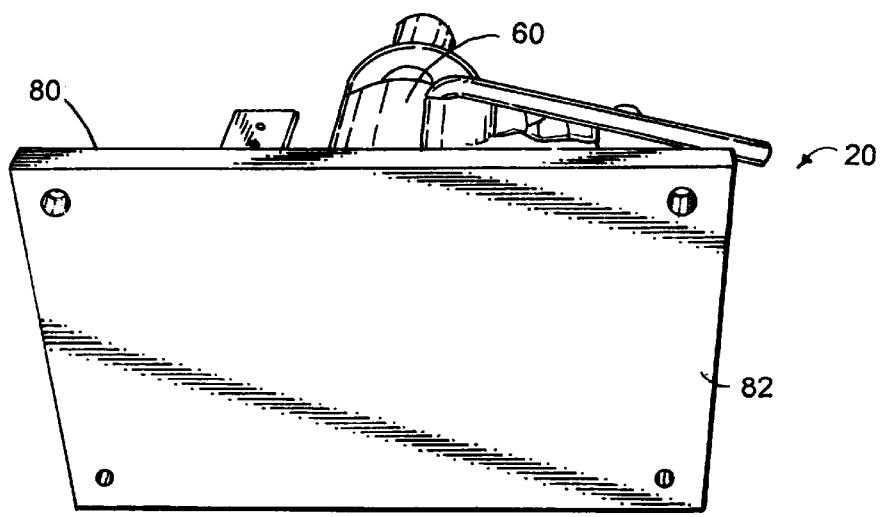
FIG. 9 is a perspective view from the bottom of the force applicator of FIG. 8.
Figures 10, 11:
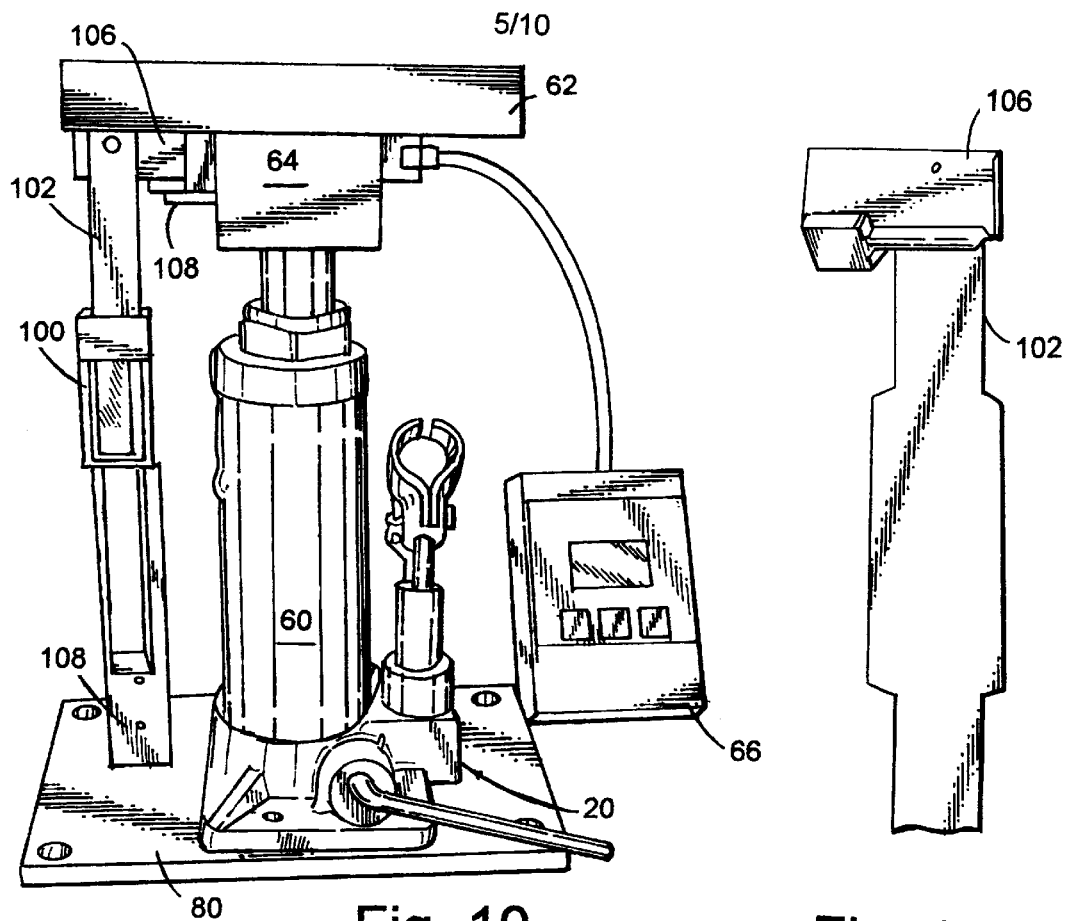
FIG. 10 is a side view of the force applicator, the force measurement gauge, and the distance measurement gauge for the apparatus of FIG. 1.
FIG. 11 is a rear view of the slide of the distance measurement gauge shown in FIG. 10.

Referring to FIG. 1, an example of the preferred embodiment of the present invention is illustrated and generally indicated by the reference numeral 10. The leaf spring test apparatus 10 generally comprises a frame 12 constructed and arranged to support a first end 14 and a second end 16 of a leaf spring 18, a force applicator 20 disposed on the frame 12 for applying a force to a predetermined area 22 of the leaf spring 18, a force measurement gauge 24 connected to the force applicator 20 for gauging the amount of force applied to the leaf spring 18 by the force applicator 20, and a distance measurement gauge 26 connected to the leaf spring 18 for gauging movement of the leaf spring upon the application of force by the force applicator 20.

Referring to FIGS. 16, 17 and 21–23, the frame 12 is preferably constructed from a rigid metal, and generally comprises a base 30, a first support 32, and a second support 34. The base 30 preferably is formed with a channel 36 within which the force applicator 20 is disposed. The first support 32 extends vertically from the base 30 to support the first end 14 or frame end of the leaf spring 18. The first support 32 preferably has a channel 38 with opposing walls and is formed as a rigid unitary structure with the base 30, and thus imitates the rigid frame of the car. The second support 34 extends vertically upward from a support region 40 of the base 30 to support the second end 16 or axle end of the leaf spring 18. The leaf spring 18 spans in a concave up orientation from the first support 32 to the second support 34. The second support 34 imitates the axle end by preferably being pivotably attached to the support region 40 allowing the second end 16 of the leaf spring 18 to extend when the force applicator 20 flexes the leaf spring 18.

Figure 14:
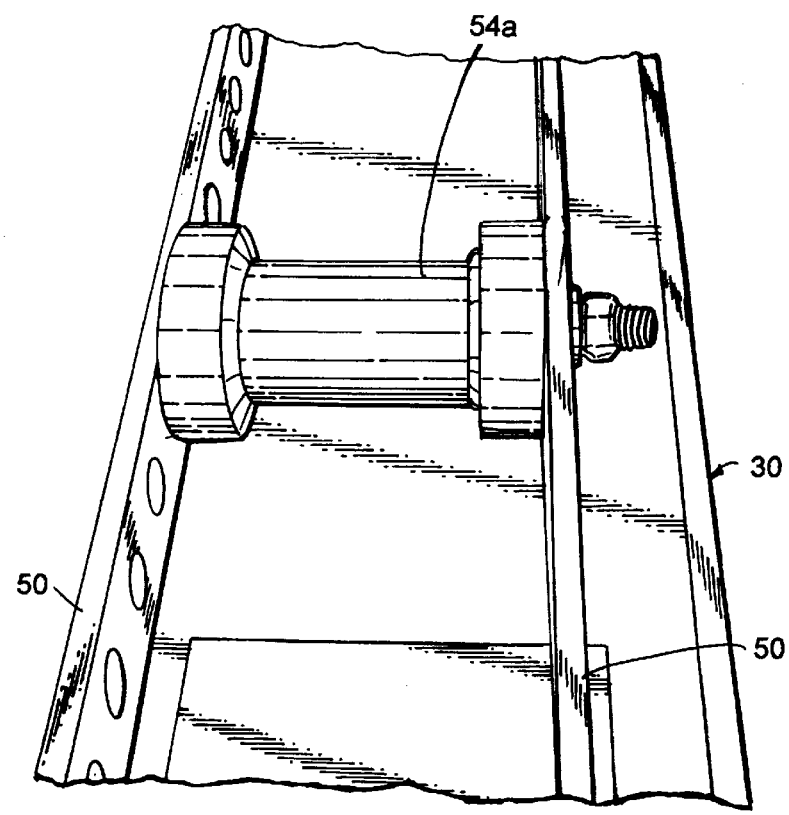
FIG. 14 is a perspective view of a large bushing extending between opposite sides of the second support for the apparatus of FIG. 1

The distance between the second support 34 and first support 32 is set by pivotably attaching the second support 34 to a desired location within the support region 40. The channel walls within the support region 40 have related set of opposing apertures 42. The second support 34 is attached to the support region 40 by extending a fastener 44 such as a pin or bolt through opposing apertures 42 in the support region 40 and through a pivot sleeve 46 in the second support 34. Additionally, the first support 32 has opposing walls with related sets of opposing apertures 48 and the second support 34 has opposing sides 35 with related sets of opposing apertures 50. A fastener 52 such as a bolt and a sleeve-like bushing 54, with appropriate spacers, extend between each of the sets of apertures 48 and 50 in the first support 32 and the second support 34. Since the fasteners 52 and bushings 54 can be attached between a number of pairs of opposing apertures, the first end 14 of the leaf spring 18 is adjustably attached to the first support 32 and the second end 16 of the leaf spring 18 is adjustably attached to the second support 34 to accommodate different sizes and shapes of leaf springs 18. Large bushings 54a, shown in FIG. 14, or small bushings 54b, shown in FIG. 15, may be used to attach different s sizes of leaf springs to the first support 32 and second support 34.

Referring to FIGS. 4–11, the force applicator 20 includes a jack 60 and a spring contact plate 62. The jack 60 is preferably a hydraulic jack having a base, a piston, and a handle. Other types of jacks and other means for applying force may be used. The force measurement gauge 26 includes a load cell 64 electrically connected to a force measurement display 66 which reports the force gauged by the load cell 64. The load cell 64 is positioned between the piston of the jack 60 and the spring contact plate 62. The spring contact plate 62 imitates a shackle having a groove sized and oriented to receive the leaf spring 18. The leaf spring 18 has an aperture 68 positioned in the predetermined area 22 or shackle location. The spring contact plate 62 may have a finger-like extension that protrudes through the aperture 68. Other means for connecting the shackle location to the jack may be used.

Since the frame or first end 14 of the leaf spring 18 does not extend, both the axle or second end 16 and the shackle location or predetermined area 22 will move when the leaf spring 18 is compressed. It is therefore desirable that the force applicator 20, specifically the jack 60, be capable of moving with the shackle location 22 of the spring 18. The jack 60 is mounted on a jack base plate 80. A jack slide plate 82 is mounted beneath the jack base plate 80 and a base slide plate 84 is mounted within the channel 36 of the base 30. The base plate 80 and slide plate 82 are sized to minimize any lateral motion of the jack 60 within the channel 36 and to allow longitudinal motion of the jack 60 as the slide plates 82 and 84 slide against each other. Therefore, when the leaf spring 18 is compressed and relaxed, the jack 60 and jack base plate 80 longitudinally slide within the channel 36 of the base 30.

Figure 12:
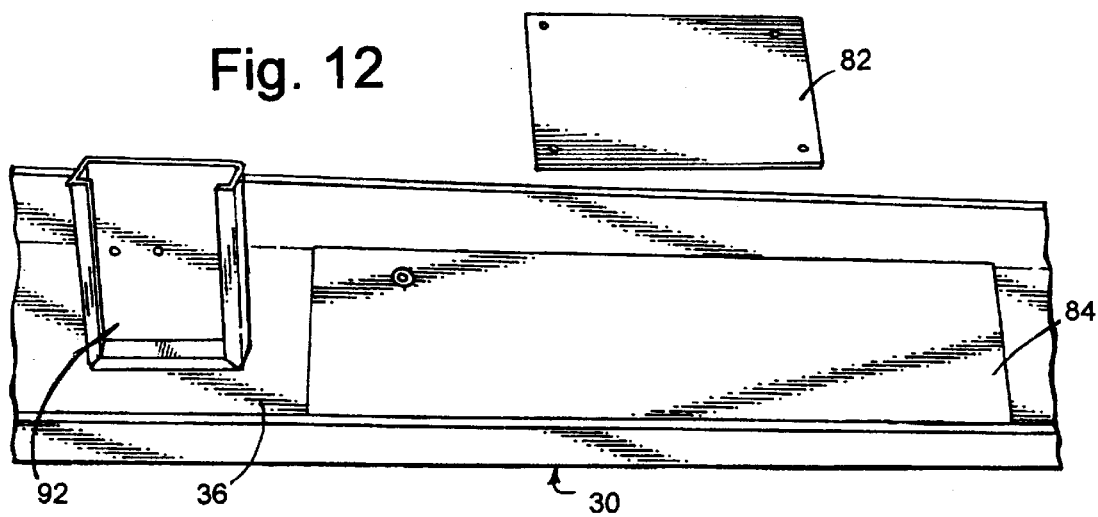
FIG. 12 is a perspective view showing the channel of the base for the apparatus of FIG. 1.
Figure 13:
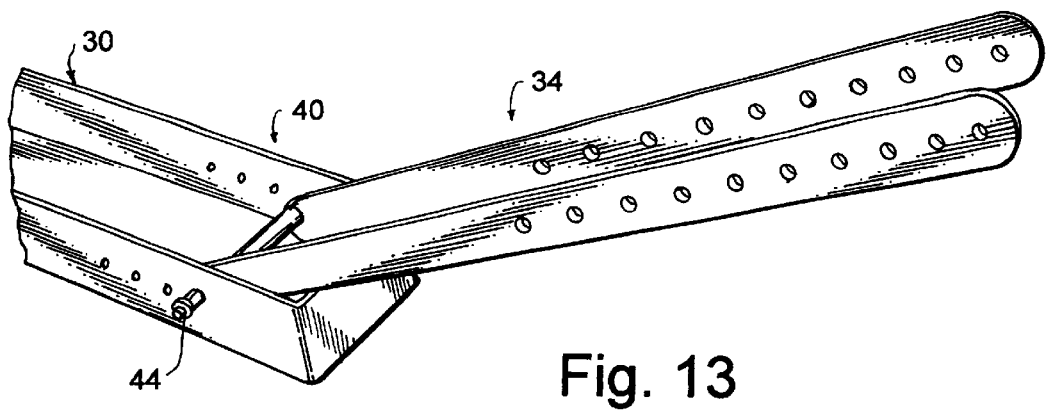
FIG. 13 is perspective view illustrating the second support pivotably attached to the base for the apparatus of FIG. 1.

As stated above, the force measurement gauge 26 includes a load cell 64 electrically connected to a force measurement display 66 which reports the force gauged by the load cell 64. The load cell 64 is shown in detail in FIGS. 18–20. Fasteners attach the load cell 64 to the bottom of the spring contact plate 62 through apertures 88. A controlled force is applied to the load cell 64 by the jack 60 through the relationship between an aperture 90 in the load cell 64 and a protrusion on the piston of the jack 60. The force measurement display 66 is preferably attached to a display mount 92, shown in FIG. 12. The force measurement display 66 is electrically connected to the load cell 64 with a sufficient length of wire to accommodate the motion of the load cell 64 with the jack 60 during the compression and relaxation of the leaf spring 18. Controls on the force measurement display 66 allow a user to turn the power on and off, to select the units of measurement, and to zero off errors found during no load.

The distance measurement gauge 26 includes a digital indicator device 100 and a slide 102. The digital indicator device 100 cooperates with and slides with respect to the slide 102 in a measured fashion to quantify the position of the load cell 64, and ultimately the leaf spring 18. The digital indicator device 100 is preferably a magnetic travel indicator that has a display readout for reporting the vertical position of the leaf spring 18 in either English or metric units. The digital indicator device 100 may be reset or initialized to 0.000 inches and can display the leaf spring compression travel length to the nearest 0.001 inches or 0.01 millimeter. The slide 102 is preferably connected to the load cell 64 using the displacement indicator arm 106. Referring to FIGS. 10 and 18–20, a dowel pin 108 is inserted into an aperture 100 in the load cell 64, and the arm 106 rests on the dowel pin 108. As the load cell 64 is raised and lowered, the dowel pin 108 raises and lowers the arm 106 and the attached slide 102. The digital indicator device 100 is mounted a fixed, predetermined distance above the jack base plate 80 through an aperture within an angled indicator support 108.

Figure 24A:
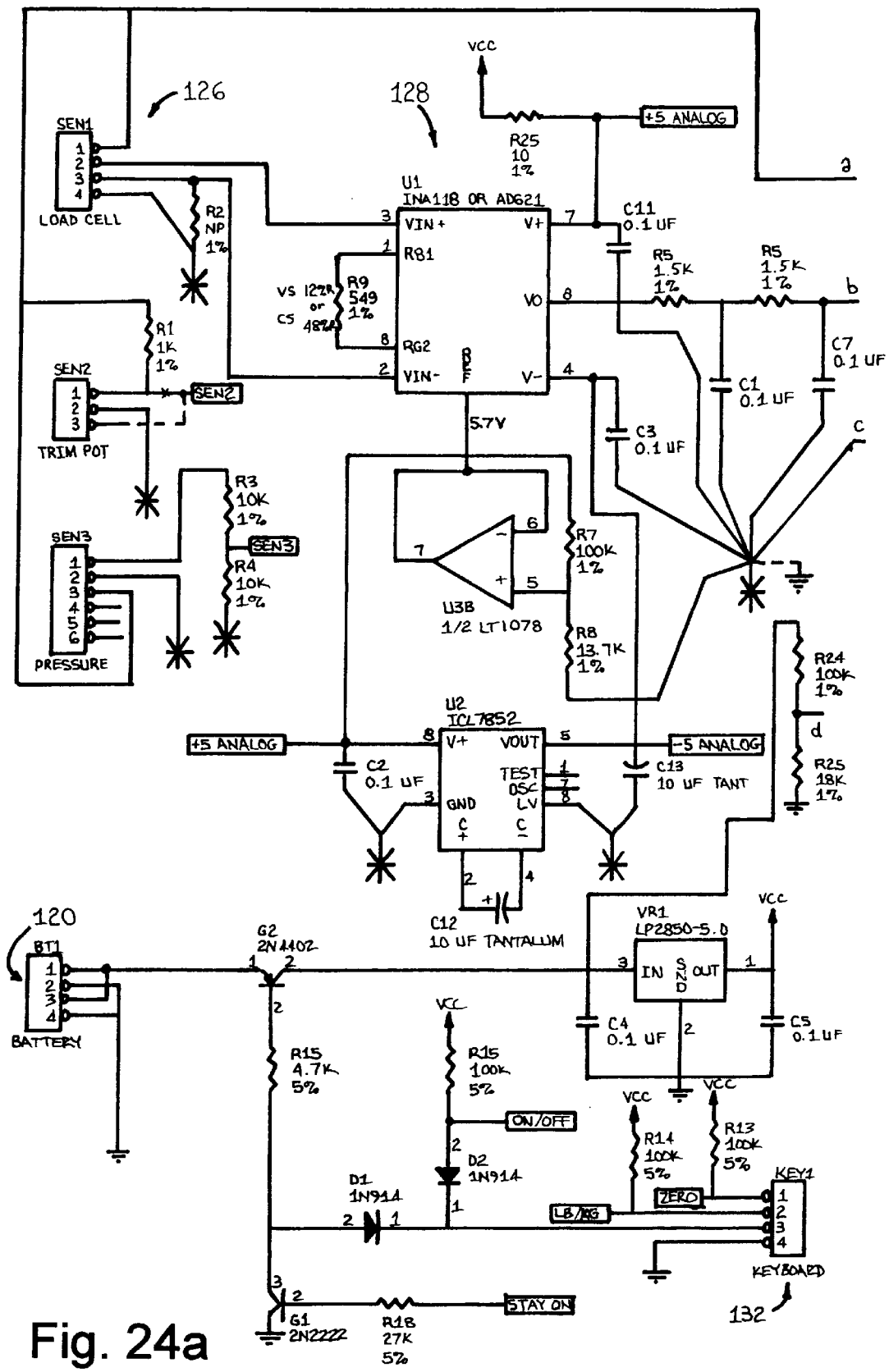
FIG. 24 is a schematic of the electronic circuitry for the apparatus of FIG. 1.

FIG. 24 is a schematic diagram of the electronic controls for the present invention. The circuitry contains a power supply, which is in this case a 9 volt alkaline or rechargeable nickel-cadmium battery 120, an EEPROM 122 for holding a program and calibration data, a microcontroller 124 for performing the operations of the program and for performing analog/digital conversions, a load cell input 126 for sensing or reading the strain gauges of the load cell 64, a signal amplifier 128 for amplifying and conditioning the signals form the load cell input 126, a LCD display output connector 130 for electrically interfacing with and driving the force measurement display 66, and a keypad input connector 132 for electrically interfacing with a keypad or other input device. The microcontroller 124 delivers over 4,000 internal counts with its 12 bit analog/digital conversions and allows the leaf spring testing apparatus 10 to automatically zero off errors found during zero-load.

Installing a leaf spring on the leaf spring test apparatus in preparation for measuring the spring rate of the leaf spring generally includes the following steps:

1. Selecting the proper bushings for the leaf spring to be tested.
2. Inserting the correct bushings into the leaf spring.
3. Carefully setting the leaf spring into the groove on the spring contact plate.
4. Holding the leaf spring so the surface of the spring that touches the plate is parallel to and is lying flat on the plate.
5. Inserting fasteners, such as bolts, through the bushing and the corresponding apertures on the frame to support the spring.
6. Tightening the nuts on the bolts that restrain the leaf spring.
7. Verifying that the leaf spring is lying flat on the spring contact plate.

Manufacturers of leaf springs often will have their own recommended procedures for testing leaf springs. These procedures may include averaging measurements from several tests and specific steps for pre-loading the spring prior to zeroing the tester. The leaf spring test apparatus may be used in a variety of these procedures. Regardless of the procedure followed, it is important to consistently perform that procedure so that accurate comparisons can be made. The method of using the leaf spring test apparatus to measure the spring rate of torsion bars may include the following steps:

1. Zeroing the leaf spring test apparatus, which may include the steps of:
   (a) Pumping the jack to apply a force to the leaf spring, wherein the force may be approximately 100 pounds;
   (b) Opening the jack valve to lower the jack; and
   (c) Zeroing the force measurement gauge and the distance measurement gauge.
2. Pumping the jack to raise the spring until the desired distance is read by the distance measurement gauge.
3. Reading the force measurement gauge.

For example, the jack may be pumped to raise the spring until the distance measurement gauge displays 1 inch. If the force measurement gauge reads 250 pounds, the spring rate for the spring is 250 pounds per inch if the spring is linear. The leaf spring is linear if another 250 pounds of force is required to raise the spring another inch.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A leaf spring test apparatus, comprising:
   (a) a frame constructed and arranged to support a leaf spring;
   (b) a force applicator disposed on said frame, said force applicator applying a force to a predetermined area of the leaf spring to cause a spring displacement;
   (c) a force measurement gauge operably positioned and arranged with respect to said force applicator to gauge the amount of force applied to the leaf spring by said force applicator; and
   (d) a distance measurement gauge operably positioned and arranged with respect to the leaf spring to gauge the spring displacement by identifying an actual or representative initial position of the leaf spring occurring prior to the application of the force to the leaf spring and a corresponding actual or representative final position of the leaf spring occurring after the application of the force to the leaf spring.

2. The leaf spring test apparatus of claim 1, wherein said frame supports a first end and a second end of a leaf spring and said frame includes:
   (a) a base having a first end and a second end;
   (b) a first support of a predetermined length extending upwardly from said first end of said base for contact with a first end of a leaf spring; and
   (c) a second support of a predetermined length extending upwardly from a support region of said base for contact with a second end of the leaf spring, said second support being a predetermined distance from said first support.

3. The leaf spring test apparatus of claim 2, wherein said first support is fixedly attached to said first end of said base and said second support is pivotably attached to said base in said support region.

4. The leaf spring test apparatus of claim 2, wherein said predetermined distance between said second support and said first support is adjustable, said second support being removably attached to said base at a plurality of locations within said support region.

5. The leaf spring test apparatus of claim 2, wherein the first end of the leaf spring is adjustably attached along said length of said first support and the second end of the leaf spring is adjustably attached along said length of said second support.

6. The leaf spring test apparatus of claim 2, wherein said base and said first support have a channel, said force applicator being disposed within said channel of said base, said first support having opposing walls and a first bushing connected to and extending between said opposing walls, said second support having opposing sides and a second bushing connected to and extending between said opposing sides.

7. The leaf spring test apparatus of claim 1, wherein said force applicator includes a jack and a spring contact plate connected to a piston of said jack, said contact plate having a groove sized and arranged to receive the spring.

8. The leaf spring test apparatus of claim 1, wherein said force applicator is slidably disposed on said frame to maintain the desired contact with the predetermined area of the leaf spring as the leaf spring is compressed and relaxed.

9. The leaf spring test apparatus of claim 1, wherein said force measurement gauge includes a load cell electrically connected to a display for reporting the force gauged by said load cell.

10. The leaf spring test apparatus of claim 9, wherein said display is digital.

11. The leaf spring test apparatus of claim 1, wherein said force applicator includes a jack and a spring contact plate connected to a piston of said jack, said contact plate having a groove sized and arranged to receive the spring, said force measurement gauge including a load cell electrically connected to a display for reporting the force gauged by said load cell.

12. The leaf spring test apparatus of claim 1, wherein said distance measurement gauge includes a digital indicator device and a slide, said digital indicator device cooperating with and sliding with respect to said slide in a measured fashion, said digital indicator device quantifying both the initial position and the final position of the leaf spring to gauge the spring displacement of the leaf spring.

13. The leaf spring test apparatus of claim 12, wherein said digital indicator device is a magnetic travel indicator.

14. The leaf spring test apparatus of claim 12, wherein said digital indicator device has a display readout for reporting the position of the leaf spring.

15. The leaf spring test apparatus of claim 12, wherein said slide is connected to the leaf spring and said digital indicator device is mounted at a predetermined height.

16. A leaf spring test apparatus, comprising:
(a) a frame constructed and arranged to support a first end and a second end of a leaf spring, said frame including:
  (i) a base having a first end and a second end;
  (ii) a first support of a predetermined length extending upwardly from said first end of said base for contact with a first end of a leaf spring, said first support being fixedly attached to said first end of said base; and
  (iii) a second support of a predetermined length extending upwardly from a support region of said base for contact with a second end of the leaf spring, said second support being a predetermined distance from said first support, said second support being pivotably attached to said base in said support region;
(b) a force applicator disposed on said frame, said force applicator applying a force to a predetermined area of the leaf spring, said force applicator including a jack and a spring contact plate connected to a piston of said jack, said contact plate having a groove sized and arranged to receive the spring, said force applicator being slidably disposed on said base to maintain the desired contact with the predetermined area of the leaf spring as the leaf spring is compressed and relaxed;
(c) a force measurement gauge for gauging the amount of force applied to the leaf spring by said force applicator, said force measurement gauge including a load cell electrically connected to a display for reporting the force gauged by said load cell, said load cell being positioned between said spring contact plate and said piston of said jack; and
(d) a distance measurement gauge for gauging movement of the leaf spring upon the application of force by said force applicator, said distance measurement gauge including a digital indicator device and a slide, said digital indicator device cooperating with and sliding with respect to said slide in a measured fashion, said digital indicator device quantifying a position of the leaf spring.

17. A leaf spring test apparatus, comprising:
(a) a frame constructed and arranged to support a first end and a second end of a leaf spring, said frame including:
  (i) a base having a first end and a second end;
  (ii) a first support of a predetermined length extending upwardly from said first end of said base for contact with a first end of a leaf spring; and
  (iii) a second support of a predetermined length extending upwardly from a support region of said base for contact with a second end of the leaf spring, said second support being an adjustable predetermined distance from said first support, said second support being removably attached to said base at a plurality of locations within said support region;
(b) a force applicator disposed on said frame, said force applicator applying a force to a predetermined area of the leaf spring, said force applicator including a jack and a spring contact plate connected to a piston of said jack, said contact plate having a groove sized and arranged to receive the spring;
(c) a force measurement gauge for gauging the amount of force applied to the leaf spring by said force applicator, said force measurement gauge including a load cell electrically connected to a display for reporting the force gauged by said load cell, said load cell being positioned between said spring contact plate and said piston of said jack; and
(d) a distance measurement gauge for gauging movement of the leaf spring upon the application of force by said force applicator, said distance measurement gauge including a digital indicator device and a slide, said digital indicator device cooperating with and sliding with respect to said slide in a measured fashion, said digital indicator device quantifying a position of the leaf spring, said digital indicator device being a magnetic travel indicator, said slide being connected to the leaf spring and said digital indicator device being mounted at a predetermined height.

18. A method for testing and measuring the spring rate of leaf springs, comprising the steps of:
(a) providing a leaf spring test apparatus including:
  (i) a frame constructed and arranged to support a leaf spring;
  (ii) a force applicator disposed on the frame, the force applicator applying a force to a predetermined area of the leaf spring to cause a spring displacement, the force applicator including a jack;

(iii) a force measurement gauge operably positioned and arranged with respect to the force applicator to gauge the amount of force applied to the leaf spring by the force applicator; and (iv) a distance measurement gauge operably positioned and arranged with respect to the leaf spring to gauge the spring displacement by identifying an actual or representative initial position of the leaf spring occurring prior to the application of the force to the leaf spring and a corresponding actual or representative final position of the leaf spring occurring after the application of the force to the leaf spring;

(b) installing the leaf spring on the leaf spring test apparatus;

(c) zeroing the distance measurement gauge of the leaf spring test apparatus;

(d) pumping the jack on the leaf spring test apparatus to apply a force to the leaf spring and raise the leaf spring a desired distance; and (e) reading the force measurement gauge to identify the amount of force applied to the leaf spring by the force applicator.

19. The method for testing and measuring the spring rate of leaf springs of claim 18, wherein the step of installing a leaf spring on a leaf spring test apparatus includes the steps of:

(a) selecting proper bushings for the leaf spring;

(b) inserting the bushings into the leaf spring;

(c) carefully setting the leaf spring into the groove on the spring contact plate;

(d) holding the leaf spring so the surface of the spring that touches the plate is parallel to and is lying flat on the plate;

(e) inserting bolts through the bushings and the corresponding apertures on the frame to support the spring;

(f) tightening the nuts on the bolts; and (g) verifying that the leaf spring is lying flat on the spring contact plate.

20. The method for testing and measuring the spring rate of leaf springs of claim 18, wherein the step of zeroing a force measurement gauge and a distance measurement gauge on the leaf spring test apparatus includes the steps of:

(a) pumping the jack to apply a force to the leaf spring;

(b) lowering the jack by opening a jack valve; and (c) zeroing the force measurement gauge and the distance measurement gauge.

21. A method for testing and measuring the spring rate of leaf springs, comprising the steps of:

(a) installing a leaf spring on a leaf spring test apparatus, including the steps of:

(i) selecting proper bushings for the leaf spring;

(ii) inserting the bushings into the leaf spring;

(iii) carefully setting the leaf spring into the groove on the spring contact plate;

(iv) holding the leaf spring so the surface of the spring that touches the plate is parallel to and is lying flat on the plate;

(v) inserting bolts through the bushings and the corresponding apertures on the frame to support the spring;

(vi) tightening the nuts on the bolts; and (vii) verifying that the leaf spring is lying flat on the spring contact plate;

(b) zeroing a leaf spring test apparatus, including the steps of (i) pumping the jack to apply a force to the leaf spring;

(ii) lowering the jack by opening a jack valve; and (iii) zeroing the force measurement gauge and the distance measurement gauge;

(c) pumping a jack on the leaf spring test apparatus to raise the leaf spring a desired distance; and (d) reading a force measurement gauge.

\* \* \* \* \*